(12) United States Patent
Sivaramakrishnan et al.

(10) Patent No.: US 10,201,831 B2
(45) Date of Patent: Feb. 12, 2019

(54) COATING INSPECTION METHOD

(71) Applicant: General Electric Company, Schenectady, NY (US)

(72) Inventors: Shankar Sivaramakrishnan, Schenectady, NY (US); Wayne Charles Hasz, Pownal, VT (US); Kristen Hall Brosnan, Schenectady, NY (US); James Edward Murphy, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 346 days.

(21) Appl. No.: 14/963,256

(22) Filed: Dec. 9, 2015

(65) Prior Publication Data

US 2017/0165708 A1   Jun. 15, 2017

(51) Int. Cl.
| | |
|---|---|
| *B05D 1/02* | (2006.01) |
| *F01D 5/28* | (2006.01) |
| *G01N 23/223* | (2006.01) |
| *G01N 21/84* | (2006.01) |
| *C23C 4/131* | (2016.01) |
| *C23C 4/134* | (2016.01) |
| *C04B 41/50* | (2006.01) |
| *C09K 11/77* | (2006.01) |
| *C23C 14/22* | (2006.01) |

(Continued)

(52) U.S. Cl.
CPC ............ *B05D 1/02* (2013.01); *C04B 41/5009* (2013.01); *C04B 41/5032* (2013.01); *C09K 11/7728* (2013.01); *C23C 4/131* (2016.01); *C23C 4/134* (2016.01); *C23C 14/221* (2013.01); *C23C 16/44* (2013.01); *C23C 30/00* (2013.01); *F01D 5/005* (2013.01); *F01D 5/288* (2013.01); *G01N 21/6456* (2013.01); *G01N 21/8422* (2013.01); *G01N 23/223* (2013.01); *F05D 2230/80* (2013.01); *F05D 2230/90* (2013.01); *F05D 2260/80* (2013.01); *G01N 2223/61* (2013.01); *Y02T 50/672* (2013.01)

(58) Field of Classification Search
None
See application file for complete search history.

(56) References Cited

U.S. PATENT DOCUMENTS

| | | | |
|---|---|---|---|
| 3,675,015 A | 7/1972 | Geib | |
| 3,930,063 A | 12/1975 | Miller et al. | |

(Continued)

FOREIGN PATENT DOCUMENTS

| | | | |
|---|---|---|---|
| EP | 0 783 043 A1 | 7/1997 | |
| EP | 1 428 902 A1 | 6/2004 | |

(Continued)

OTHER PUBLICATIONS

Feist et al., "Europium-doped yttria-stabilized zirconia for high-temperature phosphor thermometry", Journal of Materials: Design and Applications, vol. 214, No. 1, pp. 7-12, Jan. 1, 2000.

(Continued)

*Primary Examiner* — Nathan T Leong
(74) *Attorney, Agent, or Firm* — GE Global Patent Operation; Nitin Joshi

(57) ABSTRACT

Provided herein are methods and compositions which allow for efficient inspection, maintenance and repair of ceramic coatings.

33 Claims, 3 Drawing Sheets

Figure 1A:
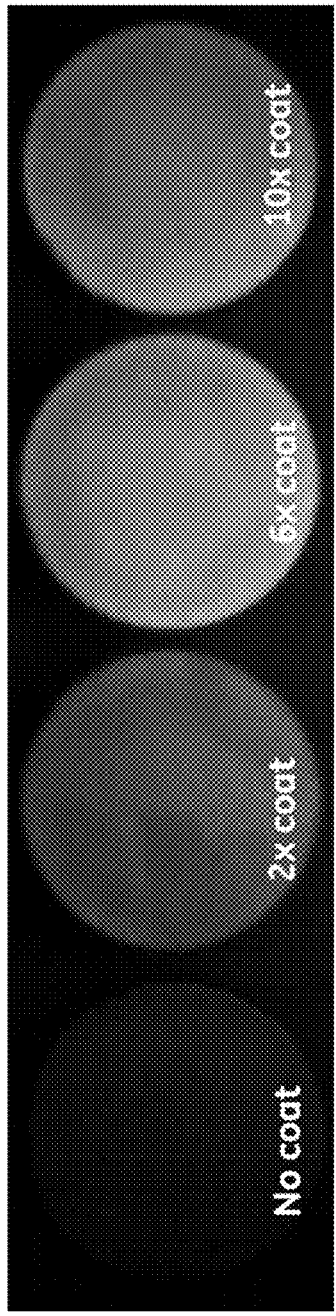

(51) Int. Cl.
*C23C 16/44* (2006.01)
*G01N 21/64* (2006.01)
*C23C 30/00* (2006.01)
*F01D 5/00* (2006.01)

(56) References Cited

U.S. PATENT DOCUMENTS

| | | | |
|---|---|---|---|
| 4,327,155 | A | 4/1982 | Hanneman |
| 4,774,150 | A | 9/1988 | Amano et al. |
| 4,922,113 | A | 5/1990 | Melancon |
| 5,087,670 | A | 2/1992 | Melancon et al. |
| 5,773,141 | A | 6/1998 | Hasz et al. |
| 5,902,670 | A | 5/1999 | Ripstein |
| 7,150,926 | B2 | 12/2006 | Strangman |
| 7,271,894 | B2 | 9/2007 | Devitt et al. |
| 7,622,195 | B2 | 11/2009 | Schlichting et al. |
| 7,807,231 | B2 | 10/2010 | Gorman et al. |
| 8,062,759 | B2 * | 11/2011 | Fu .................. C23C 28/321 428/469 |
| 8,216,689 | B2 | 7/2012 | Witz et al. |
| 8,257,559 | B2 | 9/2012 | Floyd et al. |
| 8,356,482 | B2 * | 1/2013 | Duval ................. C23C 4/18 415/200 |
| 8,470,460 | B2 | 6/2013 | Lee |
| 8,529,999 | B2 | 9/2013 | Maloney et al. |
| 8,658,291 | B2 | 2/2014 | Kirby et al. |
| 9,034,479 | B2 | 5/2015 | Nagaraj et al. |
| 2003/0115941 | A1 * | 6/2003 | Srivastava ......... G01N 21/6489 73/114.79 |
| 2004/0170849 | A1 | 9/2004 | Ackerman et al. |
| 2005/0158460 | A1 | 7/2005 | Williams |
| 2007/0134518 | A1 | 6/2007 | Feist et al. |
| 2009/0110953 | A1 | 4/2009 | Margolies |
| 2009/0122832 | A1 * | 5/2009 | Feist .................. C23C 4/12 374/161 |
| 2009/0184280 | A1 | 7/2009 | Lee |
| 2010/0081009 | A1 | 4/2010 | Nelson et al. |
| 2015/0014179 | A1 | 1/2015 | Doebber et al. |
| 2015/0126476 | A1 | 5/2015 | Cutrupi |
| 2015/0167141 | A1 | 6/2015 | Rosenzweig et al. |
| 2016/0168684 | A1 | 6/2016 | Brosnan et al. |

FOREIGN PATENT DOCUMENTS

| | | | |
|---|---|---|---|
| JP | 2001-153803 | A | 6/2001 |
| JP | 2005-232436 | A | 9/2005 |
| JP | 2012-62511 | A | 3/2012 |
| JP | 2013-129917 | A | 7/2013 |
| WO | 2014/170585 | A2 | 10/2014 |
| WO | 2015116300 | A2 | 8/2015 |

OTHER PUBLICATIONS

Marinetti et al., "Thermographic inspection of TBC coated gas turbine blades: Discrimination between coating over-thicknesses and adhesion defects", Workshop on Advanced Infrared Technology and Applications, vol. 49, Issue: 3, pp. 281-285, Jan. 2007.

B. Barber et al.,"Assessment of Damage Accumulation in Thermal Barrier Coatings Using a Fluorescent Dye Infiltration Technique", Journal of Thermal Spray Technology, vol. 8(1) Mar. 1999, pp. 79-86.

M.M. Gentleman et al.,"Concepts for luminescence sensing of thermal barrier coatings", Available online at www.sciencedirect.com, Surface & Coatings Technology 188-189 (2004) 93-100.

Kramer, S., et al.,"Infiltration-Inhibiting Reaction of Gadolinium Zirconate Thermal Barrier Coatings with CMAS Melts," Journal of the American Ceramic Society, vol. 91, No. 2, pp. 576-583 (Feb. 2008).

Zhao, H., et al., "Molten silicate interactions with thermal barrier coatings," Surface and Coatings Technology, vol. 251, pp. 74-86 (Jul. 25, 2014).

Extended European Search Report and Opinion issued in connection with corresponding EP Application No. 16202590.2 dated May 18, 2017.

Machine Translation and Notification of Reasons for Refusal issued in connection with corresponding JP Application No. 2016-231925 dated Feb. 13, 2018.

* cited by examiner

COATING INSPECTION METHOD

BACKGROUND

The disclosure relates generally to methods for protection of ceramic coatings and maintenance and inspection of such coatings.

Ceramic coatings such as thermal barrier coatings (TBCs) are typically used in components that operate at or are exposed to high temperatures. Aviation turbines and land-based turbines, for example, may include one or more components protected by ceramic coatings, including thermal barrier coatings. Under normal conditions of operation, coated components may be susceptible to various types of damage, including erosion, oxidation, and attack from environmental contaminants Current trends in the industry toward higher operating temperatures to improve efficiency are pushing component materials to extend their capability to operate in ever more aggressive environments.

A conventional coating system applied in turbine applications typically includes a ceramic coating (e.g., a thermal barrier coating (TBC)) disposed on a nickel-based superalloy substrate component (often with internal cooling passages), often including a metallic bond coating of either platinum-nickel-aluminide or MCrAlY (where M includes Ni, Co, Fe, or mixed combination) interposed between the substrate and the ceramic coating. Zirconia stabilized with yttria, known in the art as yttria-stabilized zirconia, or YSZ, is the most commonly used material for the ceramic coating. There is interest in developing new thermal barrier coating systems through microstructural and/or compositional changes of the YSZ to improve the life of turbine components.

For turbine components, environmental contaminant compositions of particular concern are those containing oxides of calcium, magnesium, aluminum, silicon, and mixtures thereof. Dirt, ash, and dust ingested by gas turbine engines, for instance, are often made up of such compounds. These oxides often combine to form contaminant compositions comprising mixed calcium-magnesium-aluminum-silicon-oxide systems (Ca—Mg—Al—Si—O), hereafter referred to as "CMAS." At turbine operating temperatures, which are high temperatures, these environmental contaminants can adhere to the hot thermal barrier coating surface, and thus cause damage to the thermal barrier coating. For example, CMAS can form compositions that are liquid or molten at the operating temperatures of the turbines. The molten CMAS composition can dissolve the thermal barrier coating, or can fill its porous structure by infiltrating the voids, cracks, channels, columns, pores, or cavities in the coating. Upon cooling, the infiltrated CMAS composition solidifies and reduces the coating strain tolerance, thus initiating and propagating cracks that may cause delamination and spalling of the coating material. This may further result in partial or complete loss of the thermal protection provided to the underlying metal substrate of the part or component. Further, spallation of the thermal barrier coating may create hot spots in the metal substrate leading to premature component failure. Premature component failure can lead to unscheduled maintenance as well as parts replacement resulting in reduced performance, and increased operating and servicing costs.

There is a need in the field for methods and materials that prevent and/or reduce damage to thermal barrier coatings and that allow for easy maintenance of thermal barrier coatings.

BRIEF DESCRIPTION

U.S. application Ser. No. 14/568,203 describes the use of protective agents to reduce and/or alleviate CMAS damage in thermal barrier coatings and such disclosure is incorporated herein by reference. The present disclosure is directed to an improvement in processes for protecting/maintaining/inspecting/repairing ceramic coatings including thermal barrier coatings.

Provided herein are methods for determination of uniformity of deposition of a material in a ceramic coating comprising:
(a) disposing one or more quantities of the material within a plurality of surface-connected openings of the ceramic coating, wherein the material comprises
   i. one or more phosphors; and
   ii. one or more protective agents;
(b) illuminating the area in which the material is disposed; and
(c) evaluating the emission intensity of light from said area.

Also provided herein are compositions that infiltrate a ceramic coating (e.g., a thermal barrier coating) and allow for protection from CMAS and also allow for visual detection of the uniformity of the infiltration of the protective compositions. The methods described herein allow for efficient inspection of ceramic-coated components quickly and easily.

DRAWINGS

Figure 1B:
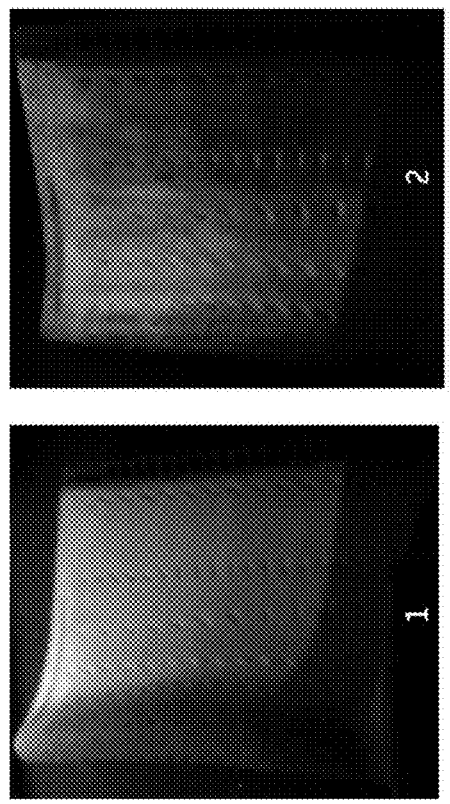

These and other features, aspects, and advantages of the present invention will become better understood when the following detailed description is read with reference to the accompanying drawings in which like characters represent like parts throughout the drawings, wherein:

FIG. 1A shows experiments with multiple coatings on buttons. $Eu^{3+}$ emission became more intense with increasing number of coatings of 2% Eu doping in a gadolinium aluminate coating. FIG. 1B shows inspection of two blades infiltrated with compositions described herein. The blades were placed under short wave UV illumination. Eu fluoresces red under 254 nm UV excitation. Blade 1 is coated evenly except around the leading edge. Blade 1 is coated more evenly than blade 2.

Figure 2:
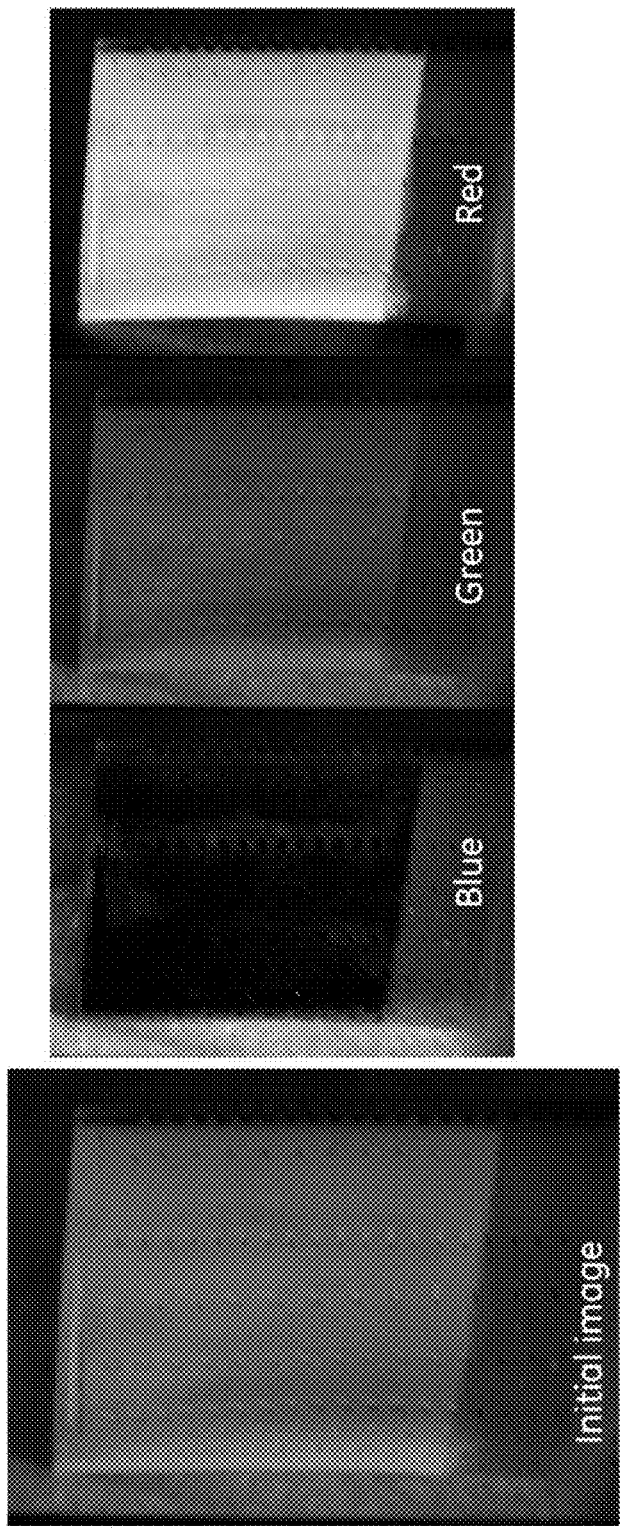

FIG. 2 shows evaluation of a blade UV fluorescence image. An initial image of Eu-fluorescence was taken with 254 nm excitation. ImageJ3D was used to split the image into component Blue-Green-Red components. An ImageJ 3D plot was used to show Red image intensity. Image Intensity varies over the blade, but the overall variation mimics the airfoil shape.

Figure 3A:
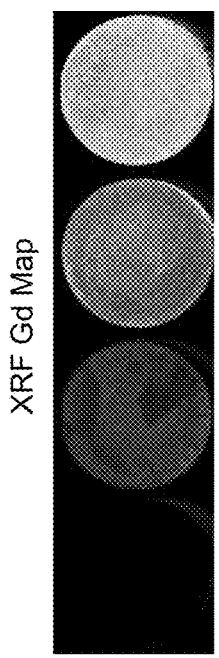
Figure 3B:
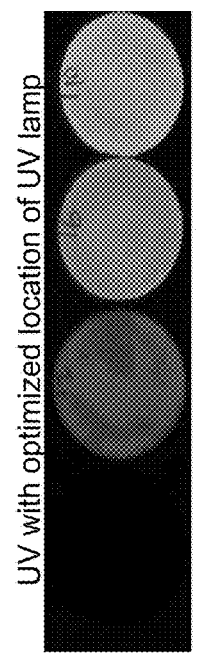
Figure 3C:
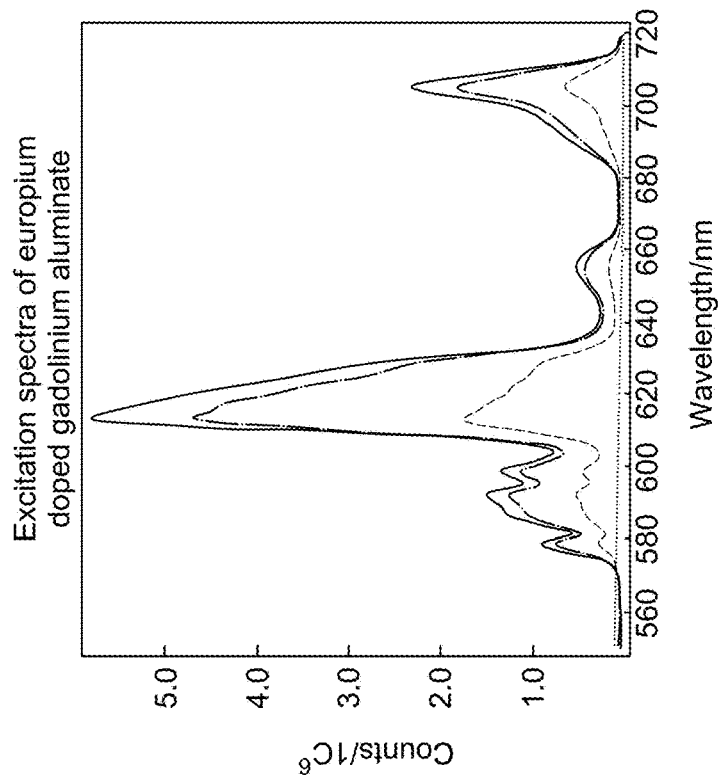

FIG. 3A and FIG. 3B show a comparison of x-ray fluorescence (XRF) versus UV data for test buttons which were illuminated with UV illumination or X-ray illumination. UV inspection compares well with XRF. FIG. 3C shows excitation spectra of europium doped with gadolinium aluminate.

DETAILED DESCRIPTION

Aspects of the present disclosure involve disposing a material within a plurality of surface-connected openings of the ceramic coating. In one group of embodiments, "disposing" a material within a plurality of surface-connected openings of the ceramic coating may be achieved by, for example, spray coating the ceramic-coated substrate. In other embodiments, "disposing" a material within a plurality of surface-connected openings of the ceramic coating involves infiltrating a composition into the openings (e.g., voids, cracks, channels, columns, pores, or cavities) of a ceramic coating such as a thermal barrier coating. Upon heating, the infiltrated composition forms a protective material, typically an oxide, that has the ability to react with CMAS rapidly. The reaction of the infiltrated material (e.g., a sacrificial oxide) with CMAS forms a material that solidifies before the CMAS can significantly penetrate the ceramic coating such as the thermal barrier coating. The infiltrated composition can additionally or alternatively react with the CMAS to increase the viscosity of the CMAS such that the CMAS cannot readily infiltrate into the TBC.

One desired aspect of infiltrating a material (comprising a protective agent and a phosphor) within a plurality of surface-connected openings of a ceramic coating is to get a uniform deposition of the protective agent into and/or onto the ceramic coating. Inspection of the infiltrated areas is desired to ensure that the application process is uniform and appropriately targeted. In the absence of a uniform dispersion of the protective agent into and/or onto the ceramic-coated substrate, damage from CMAS infiltration into regions of deficient coverage of protective agent may create hot spots in/on the ceramic-coated (e.g., TBC-coated) metal substrate leading to premature component failure.

Accordingly, provided herein are improved compositions (e.g., compositions suitable for infiltration) that comprise a protective agent (e.g., a barrier agent and/or an anti-CMAS agent which reacts with CMAS) and a phosphor in the composition. By shining a light on the infiltrated component and checking the uniformity and intensity of the light emission caused by the co-infiltrated phosphor compound, the uniformity and concentration of the application of the infiltrated composition can be determined. The methods and compositions described herein allow for identification of a region of insufficient concentration of the protective agent based on the difference in intensity of emission from the region relative to emission in other regions of the ceramic coating, thereby allowing for easy inspection of the components. Thus the present method allows for more efficient quality control and/or targeted maintenance and repair of components coated with ceramic coatings such as thermal barrier coatings.

As used herein, "surface-connected openings of the ceramic coating" are one or more of voids, cracks, channels, columns, pores, cavities, cooling passages, and the like, and are present in the ceramic coating. Said voids, cracks, channels, columns, pores, cavities, cooling passages, and the like, are a part of the ceramic-coated surface of a component, i.e., they are connected to the surface.

As used herein, the term "thermal barrier coating" refers to a coating that includes a material capable of substantially reducing heat flow to the underlying substrate of the article, that is, forming a thermal barrier. In some embodiments, the thermal barrier coating includes a material having a melting point greater than about 1000° C. In some embodiments, the thermal barrier coating includes a material having a melting point greater than about 2000° C. In some embodiments, the thermal barrier coating includes a material having a melting point in a range from about 2000° C. to about 3000° C. Examples of ceramic thermal barrier coating materials include and are not limited to various zirconias, in particular chemically stabilized zirconias (for example, metal oxides blended with zirconia), such as yttria-stabilized zirconias, ceria-stabilized zirconias, calcia-stabilized zirconias, scandia-stabilized zirconias, magnesia-stabilized zirconias, india-stabilized zirconias, ytterbia-stabilized zirconias, lanthana-stabilized zirconias, gadolinia-stabilized zirconias, as well as mixtures of such stabilized zirconias.

As used herein, a "phosphor" includes any luminescent material including a phosphorescent or a fluorescent material.

As used herein, "infiltration" may be achieved using one or more than one technique including and not limited to infiltration of liquid-based (e.g., aqueous, or solvent-based (e.g., alcohol-based (e.g., ethanol-based))) solutions or suspensions, infiltration of sol gel compositions, electrophoretic depositions (EPD), chemical or physical vapor deposition and the like.

As used herein, an "anti-calcium-magnesium-aluminum-silicon-oxide agent" or an "anti-CMAS agent" acts as a protective agent for the ceramic coating that reduces or prevents or delays CMAS-inflicted damage to the ceramic coating. An anti-CMAS agent may chemically react with liquid/molten nominal CMAS to form a solid crystalline product. The solid crystalline product has a higher melting temperature than the nominal CMAS composition so that it remains as a solid barrier to liquid/molten nominal CMAS infiltration. Alternatively, an anti-CMAS agent may increase the viscosity of liquid/molten nominal CMAS thereby reducing or preventing or delaying entry of CMAS into the ceramic coating and CMAS-inflicted damage to the ceramic coating.

An anti-CMAS agent is designed to be highly reactive to CMAS-type material, such that, at typical temperatures where CMAS is encountered in liquid form, the anti-CMAS agent rapidly reacts with the CMAS to form a solid reaction product that itself is thermally and chemically stable in the presence of liquid CMAS; or alternatively, the anti-CMAS agent reacts with molten CMAS and increases the viscosity of the molten CMAS thereby reducing or preventing or delaying ingress of CMAS into the thermal barrier coating.

For the purposes of this description, the term "nominal CMAS" refers to any CMAS composition which will cause damage to a ceramic coating (e.g., a thermal barrier coating). In an exemplary embodiment, nominal CMAS refers to the following composition, with all percentages in mole percent: 41.6% silica ($SiO_2$), 29.3% calcia (CaO), 12.5% alumina ($AlO_{1.5}$), 9.1% magnesia (MgO), 6.0% iron oxide ($FeO_{1.5}$), and 1.5% nickel oxide (NiO). It will be appreciated that the nominal CMAS composition given above is only a representative reference composition to define a benchmark for a substance's CMAS reactivity in a way that can be compared to the CMAS reactivity of other substances; use of this reference composition does not limit in any way the actual composition of ingested material that becomes deposited on the coating during operation which, of course, will vary widely in service.

As used herein, a "barrier agent" acts as a protective agent for the ceramic coating as follows. When an anti-CMAS agent is disposed (infiltrated) at the interface of the ceramic coating and the underlying bondcoat or substrate, chemical interaction between the rare-earth-bearing anti-CMAS agent and an oxide formed by the bondcoat or substrate at elevated temperature—known as a thermally-grown oxide, or TGO—can result in premature spalling of the ceramic coating. To mitigate this potential issue, some embodiments of the present invention employ a barrier agent disposed to substantially separate the anti-CMAS agent from the bondcoat or, if no bondcoat is present, from the substrate. Thus the barrier agent is interposed between substrate or bond-coated substrate and the anti-CMAS agent. The barrier agent substantially prevents chemical interaction between the anti- CMAS agent and a TGO disposed on the substrate or, if present, the bondcoat on the substrate. In some embodiments, a barrier agent comprises aluminum oxide, cerium oxide, yttrium oxide, zirconium oxide, hafnium oxide, tantalum oxide, niobium oxide, titanium oxide, or combinations thereof. Some of these oxides may, where appropriate, include a sufficient amount of stabilizer (often a rare earth element) to reduce propensity of the oxide to undergo stress-generating phase transformations during heat-up and cool-down, but the amount of rare-earth stabilizer should be sufficiently small to mitigate issues of reactivity with the aforementioned TGO. The upper limit of rare-earth stabilizer content depends on the particular element being used and the identity of the barrier agent; for example, rare earth bearing aluminate garnets tend not to dissolve alumina, and thus may contain higher amounts of rare earth material without deleterious interaction with TGO. In certain embodiments, a barrier agent tends to be less reactive towards aluminum oxide (e.g., a cerium oxide ($CeO_2$) barrier agent). In some embodiments, the barrier agent comprises less than about 40 atomic percent rare earth element content. In certain embodiments barrier agent comprises less than about 10 atomic percent rare earth element content, for example as found in the commonly used zirconia stabilized with 8 mole percent yttria ("8YSZ"). The barrier agent material need not be as reactive with CMAS as an anti-CMAS agent, because it is typically separated from contact with CMAS by the anti-CMAS agent. The function of barrier agent, then, is primarily to physically separate the anti-CMAS agent from bondcoat and/or the substrate.

Accordingly, in a first aspect, provided herein is a method comprising:
 disposing a material in a plurality of surface-connected openings of a ceramic coating, the material comprising
  i. one or more phosphors; and
  ii. one or more protective agents.

In one embodiment, the method described above further comprises ceratin inspection methods, i.e., methods for determination of uniformity of deposition of the material in the ceramic coating and such methods are described in more detail below. In additional embodiments, various methods for disposing the material in a plurality of surface-connected openings of the ceramic coating are described in more detail below.

In a second aspect, provided herein are methods for determination of uniformity of deposition of a material in a ceramic coating comprising:
 (a) illuminating a surface of the ceramic coating with a stimulant radiation, wherein the ceramic coating comprises a plurality of surface-connected openings and a material disposed in at least some of the openings, the material comprising
  i. one or more phosphors; and
  ii. one or more protective agents;
 (b) detecting an emission radiation from the material in response to the stimulant radiation; and
 (c) recording the distribution of the material within the ceramic coating based on the intensity of the detected emission radiation as a function of position on the surface.

As used herein, "recording the distribution of the material within the ceramic coating" refers to obtaining images of parts illuminated with stimulant radiation which emit radiation (e.g., fluoresce) subsequent to illumination with the stimulant radiation. Methods for obtaining such images are known in the art.

In one embodiment of the methods described herein, the ceramic coating is a thermal barrier coating.

In one embodiment of the methods described herein, after illumination of the area in which the material is disposed with a stimulant radiation, the wavelength of the light emitted from the one or more disposed phosphors is different from any wavelength of light emitted by the original ceramic coating under the same illumination. In other words, using the methods described herein, a light sensitive phosphor is co-disposed with a protective agent in the surface-connected openings of a ceramic structure and the deposition of material is checked by measuring the difference between the light emitted from the ceramic coating substantially free of phosphor (e.g., the original ceramic coating) and the ceramic coating having an effective amount of a material comprising one or more phosphors disposed in the surface connected openings of the ceramic coating.

In another embodiment, the methods further comprise identifying regions of insufficient concentration of the material based on the recorded distribution of the material, and disposing an additional quantity of the material in the regions of insufficient concentration of the material.

Determination of uniformity of the deposition of the material comprising a protective agent and a phosphor comprises, in one embodiment, illuminating with a stimulant radiation and obtaining a color image of the fluorescing part (i.e., an infiltrated substrate) and separating the image into primary colors. The camera images are processed using ImageJ software. The color images obtained using the emitted light are broken down into their primary color components, and the red intensity plotted for the specimens under observation. Image intensity in a particular wavelength, for example, red light, is examined to determine the coating amount and/or the uniformity of the coating. Fluorescence intensity can be mapped as a function of geometry to estimate concentration of the phosphor dopant across the surface of the coated article.

In one embodiment, the ceramic coating, subsequent to deposition of a material comprising a protective agent and a phosphor, is illuminated with a stimulant radiation which is ultra-violet (UV) light. It will be understood that any suitable form of illumination/stimulant radiation may be used and may be matched to any suitable phosphor present in the disposed material. Contemplated within the scope of embodiments presented herein is X-ray fluorescence, that is, illumination of the ceramic coating, subsequent to deposition of a material comprising a protective agent and a phosphor, with high-energy X-rays or gamma rays and evaluating the emission of secondary (fluorescent) x-rays. In short, "illuminating" or "illuminating with a stimulant radiation" as used herein means supplying any form of electromagnetic radiation, such as but not limited to gamma rays, X-rays, visible light, near infrared light, ultraviolet light and the like. Similarly, the term "light" as used herein means any form of electromagnetic radiation and is not limited to visible wavelengths.

In certain embodiments, the phosphor is present in the material in an amount from about 0.1% to about 5% by weight of the material. In other embodiments, the phosphor is present in the material in an amount from about 0.1% to about 2.5% by weight of the material.

The phosphor comprises a host and an activator, typically chosen to provide a phosphor that avoids substantial overlap with emissions from any other phosphor that may be present in the ceramic coating itself. The host is typically a wide band gap material and the activator is an ion where the excitation and emission occur. The activator is typically chosen so that the emitted light is in the visible range, near infrared or near-UV range. The host holds the activator ions in place so that the activator ions do not cluster and undergo concentration quenching. By way of example, an activator for a phosphor described herein may comprise one or more of copper, added in concentration of 5 ppm to 20 mol % copper-activated zinc sulfide, silver, added to zinc sulfide, europium(II) added to strontium aluminate, cerium, added to yttrium aluminium garnet, and the like. By way of example, a host for an activator for any phosphor described herein may comprise one or more of oxides, nitrides, oxynitrides, sulfides, selenides, halides or silicates of zinc, cadmium, manganese, aluminium, silicon, sulfur, phosphorous, or various rare earth metals.

In one group of embodiments, the phosphor comprises one or more of europium, tungsten, molybdenum, lead, boron, titanium, manganese, uranium, chromium, terbium, dysprosium, yttrium, cerium, gadolinium, lanthanum, phosphorous, oxygen, lutetium or nitrogen.

In a specific embodiment, the phosphor includes europium. In one instance, the europium is present in the material in an amount from about 0.1% to about 5% by weight of the material. Alternatively, the europium is present in the material in an amount from about 0.1% to about 2.5% by weight of the material.

In one group of embodiments, the protective agent includes a barrier agent, an anti-calcium-magnesium-aluminum-silicon-oxide (CMAS) agent, or a combination thereof. In some of such embodiments, the material comprises a barrier agent and a phosphor. In some other such embodiments, the material comprises an anti-CMAS agent and a phosphor.

In one embodiment of the methods described herein, in a first quantity, the disposed material comprises one or more barrier agents; and in a second quantity, the disposed material comprises one or more anti-CMAS agents.

In one embodiment of the methods described herein, in a first quantity, the disposed material comprises one or more barrier agents and a first phosphor, and in a second quantity, the disposed material comprises one or more anti-CMAS agents and a second phosphor; wherein, after illumination of the area in which the one or more quantities of the material is disposed with a stimulant radiation, the wavelength of the light emitted from the first phosphor is different from the wavelength of light emitted by the second phosphor. Further, the wavelengths of light emitted by the first and second phosphors are different from any wavelengths of light which may be emitted by the ceramic coating itself (e.g., where the ceramic coating itself comprises a phosphor).

Also contemplated herein are embodiments wherein the disposed material comprises the barrier agent and the anti-CMAS agent in the same composition along with one or more phosphors. Further, in certain instances, an anti-CMAS agent or a barrier agent may itself be a phosphor as well.

In one group of embodiments, the protective agent is an anti-CMAS agent comprising one or more rare earth elements or alkaline earth elements, or a combination thereof. In some of such embodiments, the one or more rare earth elements are selected from the group consisting of lanthanum, neodymium, erbium, cerium, and gadolinium. In some of such embodiments, the one or more alkaline earth elements are selected from the group consisting of beryllium, magnesium, calcium, strontium, barium, and radium.

In one group of embodiments, the anti-CMAS agent comprises a nitride, an oxide, or combinations thereof. In some of such embodiments, the anti-CMAS agent comprises nitrides of rare earth elements or alkaline earth elements, oxides of rare earth elements or alkaline earth elements, or combinations thereof. In another group of embodiments, the anti-CMAS agent further comprises zirconium, hafnium, titanium, tantalum, or niobium.

In one embodiment, the anti-CMAS agent comprises a rare-earth element, oxygen, and an element selected from the group consisting of tantalum and niobium. In another embodiment, the anti-CMAS agent has a nominal formula $A_3BX_7$, wherein A comprises a rare earth metal element, B comprises tantalum, niobium, or combinations thereof, and X comprises oxygen, fluorine, or combinations thereof.

In one embodiment, the anti-CMAS agent has a weberite crystal structure and comprises gadolinium, oxygen, and at least one element selected from the group consisting of tantalum and niobium. In another embodiment, the anti-CMAS agent comprises an oxide having the nominal formula $A_{1-x}B_xZr_{4-y}D_y(PO_4)_z$;

wherein A and B are selected from the group consisting of alkaline earth metals and rare earth metals, D is hafnium or titanium, x is a number from 0 to 1; y is a number from 0 to 4; and z is 3 or 6.

In one embodiment, the anti-CMAS agent comprises $MZr_4(PO_4)_6$, wherein M comprises at least one alkaline earth metal. In another embodiment, the anti-CMAS agent comprises $Ca_xSr_{1-x}Zr_4(PO_4)_6$, wherein x is a number from 0 to 1. In some of such embodiments, the anti-CMAS agent comprises $CaZr_4(PO_4)_6$, $Sr Zr_4(PO_4)_6$, $Ca_{0.5}Sr_{0.5}Zr_4(PO_4)_6$, or combinations thereof.

In one embodiment, the anti-CMAS agent has a perovskite crystal structure and comprises (a) a rare earth element, (b) tantalum, niobium, or a combination of tantalum and niobium, and (c) oxygen. In another embodiment, the anti-CMAS agent comprises gadolinium, tantalum, and oxygen.

In one embodiment, the anti-CMAS agent comprises a compound having a scheelite, fergusonite, or wolframite crystal structure, and having a nominal formula $ABX_4$, wherein A comprises a rare-earth element, B comprises tantalum, niobium, or a combination of tantalum and niobium, and X comprises oxygen, nitrogen, or a combination of nitrogen and oxygen. In some of such embodiments, A comprises yttrium, gadolinium, lanthanum, neodymium, ytterbium, or a combination thereof.

In one group of embodiments, the protective agent includes a barrier agent comprising aluminum oxide, hafnium oxide or cerium oxide, or a combination thereof. In some of such embodiments, the barrier agent comprises $Al_2O_3$, $HfO_2$, $Ce_2O_3$, or a combination thereof. In some other such embodiments, the barrier agent comprises $Ce_2O_3$.

In certain embodiments, the protective agent is selected from the group consisting of $GdAlO_3$, $Gd_3NbO_7$, and $GdTa_3O_9$.

In certain embodiments, the material disposed within the surface connected openings of the ceramic coating comprises 1.5 weight % of $Eu_2O_3$ by total weight of the material; in such embodiments, the europium oxide is a phosphor and the material optionally further comprises an anti-CMAS agent, or a barrier agent, or a combination thereof.

In certain embodiments, the material disposed within the surface connected openings of the ceramic coating comprises $Gd_{0.98}Eu_{0.02}AlO_3$; where the material includes a phosphor and an anti-CMAS agent.

In one instance, disposing the material within the ceramic coating comprises infiltrating the surface connected openings of the ceramic coating with a liquid. In such embodiments, the liquid comprises a carrier fluid and a plurality of particles suspended within the carrier fluid. Alternatively, the liquid comprises a solvent and a solute dissolved in the solvent.

In some embodiments, infiltrating the material as a liquid further comprises volatilizing the liquid to form a residue disposed in the surface-connected openings of the ceramic coating.

In another aspect, provided herein is a ceramic coating comprising a protective agent and a phosphor disposed in its surface-connected openings. In one embodiment, the ceramic coating is a thermal barrier coating. In some embodiments, the protective agent is a barrier agent, an anti-calcium-magnesium-aluminum-silicon-oxide (CMAS) agent, or a combination thereof, where the protective agent is as described above.

The ceramic coatings (e.g., thermal barrier coatings) are typically deposited or otherwise formed on a bond coating (if present) or on the substrate directly by any of a variety of conventional techniques, including vapor deposition, such as physical vapor deposition (PVD), electron beam physical vapor deposition (EBPVD); plasma spray, such as air plasma spray (APS), suspension plasma spray (SPS), and vacuum plasma spray (VPS); other thermal spray deposition methods such as high velocity oxy-fuel (HVOF) spray, detonation, or wire spray; chemical vapor deposition (CVD), sol-gel method, or combinations of two or more of the aforementioned techniques.

Ceramic coatings, including thermal barrier coatings, typically comprise surface connected openings such as pores, channels or other cavities that, during subsequent operation, are infiltrated by molten environmental contaminants, such as, CMAS. In some instances, such pores, channels, or cavities are created by environmental damage or the normal wear and tear during operation of the ceramic coatings (e.g., thermal barrier coatings). In some instances, the surface openings in a ceramic coating arise from the deposition processes. For example, thermal barrier coatings deposited by (air) plasma spray techniques may comprise a sponge-like porous structure of open pores in at least the surface of the coating. Similarly, thermal barrier coatings that are deposited by physical (e.g., chemical) vapor deposition techniques may comprise a porous structure including a series of columnar grooves, crevices or channels in at least the surface of the coating. While the porous structure provides for strain tolerance by ceramic coatings during thermal cycling, and further provides for stress reduction due to the differences between the coefficient of thermal expansion (CTE) of the coating and the CTE of the underlying bond coat layer/substrate, the inherent porous structure is also vulnerable to infiltration by molten environmental contaminants such as CMAS.

The type of substrate may depend in part on the turbine component. Non-limiting examples of suitable substrates include metals, metal alloys, or combinations thereof. In certain embodiments, the substrate includes an alloy of nickel, cobalt, iron, or combinations thereof. For example, the substrate may include a high temperature, heat-resistant alloy, e.g., a superalloy. Non-limiting examples of suitable high temperature nickel-based alloys include Inconel®, Nimonic®, Rene® (e.g., Rene® 80, Rene® 95 alloys), Udimet®, or combinations thereof. By way of non-limiting examples, the substrate may comprise one or more of nickel-base superalloys, cobalt-base superalloys, and ceramic matrix composites, and the like.

The optional bond coating may be formed from a metallic oxidation-resistant material that protects the underlying substrate and enables the thermal barrier coating to more tenaciously adhere to substrate. Bond coats provide functionality—adhesion promotion and oxidation resistance. Suitable materials for the bond coating include $M_1CrAlY$ alloy powders, where $M_1$ represents a metal such as iron, nickel, platinum or cobalt. Bondcoats are especially useful when applied to a metallic substrates comprising superalloys. In other embodiments, bondcoats comprise silicide compounds or elemental silicon, which are often associated with ceramic-based substrates, such as silicon carbide-reinforced silicon carbide ceramic matrix composites (CMC's). Bond coatings are applied using any of various coating techniques known in the art, such as plasma spray, thermal spray, chemical vapor deposition, or physical vapor deposition. Non-limiting examples of suitable bond coat materials include metal aluminides such as nickel aluminide, platinum aluminide, or combinations thereof. The bond coating may have a thickness in the range of from about 25 microns to about 500 microns.

As used herein, a material is considered resistant to CMAS infiltration in this context if it is more resistant, relative to 8 mole percent yttria stabilized zirconia (8YSZ), to infiltration by liquid CMAS having the nominal CMAS composition described previously herein at a temperature of 1300 degrees Celsius. It will be appreciated that the 1300 degree Celsius temperature and the nominal CMAS composition represent a reference temperature and a reference composition to define a benchmark for the material's CMAS resistance in a way that can be compared to the CMAS resistance of 8YSZ; use of these reference values does not limit in any way the actual temperature at which any ceramic-coated article may operate or the actual composition of ingested material that becomes deposited on the coating during operation, both of which, of course, will vary widely in service.

The methods described herein are suitable for protection and/or inspection of a wide variety of components (e.g., turbine engine components) that are operated at, or exposed to, high temperatures. Non-limiting examples of suitable turbine engine components include turbine airfoils such as blades and vanes, turbine shrouds, turbine nozzles, buckets, combustor components such as liners and deflectors, heat shields, augmentor hardware of gas turbine engines, and the like. The material comprising a protective agent and a phosphor is disposed over a portion or over all of the metal substrate. By way of illustration only, with regard to airfoils such as blades, the material is typically used to protect, cover or overlay portions of the metal substrate of the airfoil other than solely the tip thereof, for example, the thermal barrier coatings cover the leading and trailing edges and other surfaces of the airfoil.

EXAMPLES

Europium nitrate hexahydrate was added to an anti-CMAS agent solution (1M $GdAlO_3$ from aqueous nitrates) such that the molar ratio of Eu/Gd was 0.02. The solution was applied uniformly to various TBC coated specimens. The applications were repeated as needed with an 80 degree C. air dry, and 700 degree C. air bake to create a set of samples with various loadings of the phosphor doped anti-CMAS agent. Fluorescence of the agent was observed using a 254 nm ultraviolet illumination source (UVGL-25, 4 w 254/365 nm, PN 95-0021-12, UVP LLC, Upland CA, www.uvp.com) and detected using a Nikon D80 camera with a AF-S 18-135 mm Nikkor lens with fixed exposure conditions. The camera images were processed using ImageJ software. The color images obtained using the emitted light were broken down into their primary color components, and the red intensity plotted for the specimens under observation.

In the first example, PVD TBC coated buttons were coated with 0, 2, 6, or 10 solution applications. UV illumination of the buttons caused the infiltrated phosphor to emit light within the expected wavelength region, allowing determination of coating uniformity, coverage and concentration on the buttons.

In a second example, a PVD TBC-coated turbine blade was masked and coated with up to 10 solution applications in specific areas. UV illumination of the blade caused the infiltrated phosphor to emit light within the expected wavelength region, allowing determination of coating uniformity, coverage and concentration on the blade airfoil.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for determination of uniformity of deposition of a material in a thermal barrier coating, the method comprising:
   (a) illuminating a surface of the thermal barrier coating with a stimulant radiation, wherein the thermal barrier coating is disposed on a superalloy substrate or on a metallic bond coated superalloy substrate, and wherein the thermal barrier coating comprises a plurality of surface-connected openings at the surface and the material disposed in at least some of the surface-connected openings, the material comprising
      i. one or more phosphors; and
      ii. one or more protective agents;
   (b) detecting an emission radiation from the material in response to the stimulant radiation; and
   (c) recording the distribution of the material within the thermal barrier coating based on the intensity of the detected emission radiation as a function of position on the surface.

2. The method of claim 1, wherein, after illumination of the area in which the material is disposed with a stimulant radiation, the wavelength of the light emitted from the one or more disposed phosphors is different from any wavelength of light emitted by the original thermal barrier coating under the same illumination.

3. The method of claim 1, further comprising identifying regions of insufficient concentration of the material based on the recorded distribution of the material, and disposing an additional quantity of the material in the regions of insufficient concentration of the material.

4. The method of claim 1, wherein the stimulant radiation is ultra-violet (UV) light.

5. The method of claim 1, wherein the phosphor is present in the material in an amount from about 0.1% to about 5% by weight of the material.

6. The method of claim 1, wherein the phosphor comprises a host and an activator.

7. The method of claim 6, wherein the host is alumina.

8. The method of claim 7, wherein the activator is europium.

9. The method of claim 1, wherein the phosphor comprises one or more of europium, tungsten, molybdenum, lead, boron, titanium, manganese, uranium, chromium, terbium, dysprosium, yttrium, cerium, gadolinium, lanthanum, phosphorous, oxygen, lutetium or nitrogen.

10. The method of claim 9, wherein the phosphor contains europium.

11. The method of claim 10, wherein the europium is present in the material in an amount from about 0.1% to about 2.5% by weight of the material.

12. The method of claim 1, wherein the protective agent is a barrier agent, an anti-calcium-magnesium-aluminum-silicon-oxide (CMAS) agent, or a combination thereof.

13. The method of claim 12, wherein, in a first quantity, the disposed material comprises one or more barrier agents; and in a second quantity, the disposed material comprises one or more anti-CMAS agents.

14. The method of claim 13, wherein in a first quantity, the disposed material comprises one or more barrier agents and a first phosphor, and in a second quantity, the disposed material comprises one or more anti-CMAS agents and a second phosphor; wherein, after illumination of the area in which the one or more quantities of the material is disposed with a stimulant radiation, the wavelength of the light emitted from the first phosphor is different from the wavelength of light emitted by the second phosphor.

15. The method of claim 12, wherein the anti-CMAS agent comprises one or more rare earth elements or alkaline earth elements, or a combination thereof.

16. The method of claim 15, wherein the one or more rare earth elements are selected from the group consisting of lanthanum, neodymium, erbium, cerium, and gadolinium.

17. The method of claim 15, wherein the one or more alkaline earth elements are selected from the group consisting of beryllium, magnesium, calcium, strontium, barium, and radium.

18. The method of claim 15, wherein the anti-CMAS agent comprises a nitride, an oxide, or combinations thereof.

19. The method of claim 15, wherein the anti-CMAS agent further comprises zirconium, hafnium, titanium, tantalum, or niobium.

20. The method of claim 12, where in the protective agent comprises a barrier agent and the barrier agent comprises aluminum oxide, hafnium oxide or cerium oxide, or a combination thereof.

21. The method of claim 12, where in the barrier agent comprises $Al_2O_3$, $HfO_2$, $Ce_2O_3$, or a combination thereof.

22. The method of claim 1, wherein the material comprises a barrier agent and a phosphor.

23. The method of claim 1, wherein the material comprises an anti-CMAS agent and a phosphor.

24. The method of claim 23, wherein the anti-CMAS agent is physically separated from the
   (i) bond coat, if bond coat is present, or
   (ii) substrate, if no bond coat is present.

25. The method of claim 1, wherein the protective agent is selected from the group consisting of $GdAlO_3$, $Gd_3NbO_7$, and $GdTa_3O_9$.

26. The method of claim 1, wherein the material comprises 1.5 weight % of $Eu_2O_3$ by total weight of the material.

27. The method of claim 1, wherein the material comprises $Gd_{0.98}Eu_{0.02}AlO_3$.

28. The method of claim 1, wherein disposing the material within the thermal barrier coating comprises infiltrating the surface connected openings of the thermal barrier coating with a liquid.

29. The method of claim 28, wherein the liquid comprises a carrier fluid and a plurality of particles suspended within the carrier fluid.

30. The method of claim 28, wherein the liquid comprises a solvent and a solute dissolved in the solvent.

31. The method of claim 28, further comprising volatilizing the liquid to form a residue disposed in the surface-connected openings of the thermal barrier coating.

32. A method for determination of uniformity of deposition of a material in a thermal barrier coating, the method comprising:
  (a) illuminating a surface of the thermal barrier coating with a UV radiation, wherein the thermal barrier coating is disposed on a superalloy substrate or on a metallic bond coated superalloy substrate, and wherein the thermal barrier coating comprises a plurality of surface-connected openings at the surface and the material disposed in at least some of the surface-connected openings, the material comprising
    i. phosphorescent alumina; and
    ii. one or more protective agents;
  (b) detecting an emission radiation from the material in response to the UV radiation; and
  (c) recording the distribution of the material within the thermal barrier coating based on the intensity of the detected emission radiation as a function of position on the surface.

33. The method of claim 32, wherein the phosphorescent alumina comprises europium dopant.

* * * * *